United States Patent [19]

Schmitt et al.

[11] Patent Number: 4,493,911

[45] Date of Patent: Jan. 15, 1985

[54] NONADHESIVE IMPRESSION MATERIAL

[75] Inventors: Werner Schmitt; Robert Purrmann, both of Starnberg; Peter Jochum, Hechendorf, all of Fed. Rep. of Germany

[73] Assignee: Espe Fabrik pharmazeutischer Praparate, GmbH, Seefeld, Fed. Rep. of Germany

[21] Appl. No.: 559,703

[22] Filed: Dec. 9, 1983

[30] Foreign Application Priority Data

Dec. 16, 1982 [DE] Fed. Rep. of Germany ....... 3246654

[51] Int. Cl.$^3$ ............... C08K 5/20; C08L 79/00; A61K 6/10
[52] U.S. Cl. ............................ 523/109; 523/1; 433/214; 524/221; 524/724
[58] Field of Search ............ 523/109, 1; 524/724, 524/221

[56] References Cited

U.S. PATENT DOCUMENTS

| | | | |
|---|---|---|---|
| 2,991,265 | 7/1961 | Clark | 524/221 |
| 3,453,242 | 7/1969 | Schmitt | 521/120 |
| 3,699,041 | 10/1972 | Sanderford | 524/221 |
| 3,751,395 | 8/1973 | Schmitt | 523/109 |
| 4,093,555 | 6/1978 | Schmitt | 523/1 |

Primary Examiner—C. Warren Ivy
Attorney, Agent, or Firm—Burns, Doane, Swecker and Mathis

[57] ABSTRACT

Impression materials based on cross-linked aziridino-polyester compounds which tend to adhere to the surface to be reproduced, are made nonadhesive by the addition of 1-15% by weight of oleic acid ethanolamide with respect to the aziridino-polyether component, and may thereafter be more easily and smoothly released from the object to be reproduced.

10 Claims, No Drawings

NONADHESIVE IMPRESSION MATERIAL

BACKGROUND OF THE INVENTION

1. Field of the Invention

The present invention relates to impression material, and the use thereof.

2. Description of the Prior Art

Impression materials having good rubber elasticity and high ultimate tensile strengths, which are obtained from the use of cross-linkable starting compounds, and which polymerize rapidly and completely at room temperature, are known from U.S. Pat. No. 3,453,242. These materials are based on polyethers with aziridine terminal groups, have a minimum molecular weight of 1000 and contain on the average more than one ethylenimine residue per molecule. They have been used for a long period of time with great success, in particular in the field of dentistry, for preparing molds of the jaw in the preparation of prostheses and similar tooth replacements.

The aforementioned aziridine polyethers are worked into a paste with plasticizers, fillers, pigments and taste improvers, which are then mixed with the polymerization initiators described in the above cited patent, whereupon the mixture is applied to the surface to be reproduced. Following cross-linking, the hardened elastic mass may be removed, whereby very accurate moldings are obtained.

A disadvantage of these impression materials consists of the fact that they have a certain adhesive effect, and that consequently the polymerized material is occasionally difficult to remove from the object to be produced. Especially when used as a dental impression material, it may occur on occasion that the imprint is somewhat difficult to remove from the mouth, as the impression material exhibits a certain adhesion to natural teeth, synthetic plastic teeth and also metal crowns. It may even occur in individual cases that particularly exposed parts, such as for example extensions into interdental spaces, are torn off during the removal of the impression.

In order to prevent adhesive effects, it is known to add silicones, waxes, metal soaps, certain polymers or talcum and mica as separating materials to the different molding materials. However, these additions are entirely without effect on the abovementioned materials based on aziridino compounds, or they alter the properties of the impression material detrimentally to such an extent that it becomes useless. Thus, the impression material may be rendered hydrophobic so strongly that particularly when used as a dental impression material, it no longer flows adequately onto the wet parts of the mouth, thereby impairing the molding accuracy, or the swelling or shrinking behavior of the elastic moldings are affected negatively to the extent that the dimensional stability of the impression obtained is no longer assured over a longer period of time.

BRIEF SUMMARY OF THE INVENTION

The present invention is a nonadhesive impression material comprising a cross-linkable aziridino polyether compound and oleic acid ethanolamide. The present invention also includes the use of such material for making a dental impression.

DETAILED DESCRIPTION OF THE INVENTION

As stated above, it has now been discovered that by the addition of an oleic acid ethanolamide, this adhesive nature may be eliminated, without detrimentally affecting other positive properties of the impression material. This is even more surprising, since structurally related substances, such as for example palmitic acid ethanolamide or lauric acid ethanolamide, do not exhibit the anti-adhesive effect according to the invention in such impression materials.

The anti-adhesive effect appearing as the result of the addition according to the invention is obtained by adding an adhesion reducing amount, preferably 1–15% by weight of oleic acid ethanolamide, and more preferably 2–10% by weight of oleic acid ethanolamide, with respect to the weight of the aziridino-polyether.

Usually, the aziridino-compound is worked into a paste together with plasticizers, fillers, pigments and taste improvers. This paste may contain the oleic acid ethanolamide. Suitable plasticizers are, for example, phthalic acid ester, acylated citric acid esters, polyglycols, dibenzyltoluene, or polyethoxylated sorbitan esters being suitable as plasticizers.

The fillers in the case of the impression materials of the present invention that are readily released from the object to be reproduced, may consist as usual of all neutral and basic types, such as for example diatomaceous earth, calcium carbonate, calcium silicate, or magnesium oxide.

An initiators for the polymerization of the aziridino compound, preferably sulfonic acid esters, and more preferably, dichlorobenzenesulfonic acid methylester, are used. The initiators are added in a quantity of 1–10% by weight with respect to the aziridine compound. Preferably, the initiator of the impression material is used in the form of its mixture with plasticizers, whereby the same plasticizers are applicable as listed above for the impression paste. For viscosity control, the addition of fillers may be useful, e.g. pyrogenic silica and/or diatomaceous earth.

The oleic acid ethanolamide employed according to the invention is preferably added to the aziridino-polyether component of the impression material, which is then mixed with the initiator component shortly prior to the application of the material to the surface to be reproduced. The mixture is applied with a tray to the jaw in the mouth cavity. After a few minutes the cross-linking and hardening of the rubber elastic molding has taken place, after which the impression may be removed from the jaw smoothly and without difficulty while rendering a complete and accurate impression of the jaw, together with fine structural features.

To obtain a more complete understanding of the present invention, the following examples and comparative example are set forth. However, it should be understood that the invention is not limited to the specific details set forth in the following examples.

EXAMPLE 1

An impression paste is prepared by mixing 100 g of a polyether with aziridino terminal groups (average molecular weight 3600), the preparation of which is described in Example 13 of U.S. Pat. No. 3,454,242, with 5 g of dibutylphthalate and 50 g of diatomaceous earth. Two grams of oleic acid ethanolamide are further added to the material.

The initiator paste is prepared by kneading together 80 g of dioctylphthalate, 20 g of 2,5-dichlorobenzenesulfonic acid methylester and 16 g of pyrogenic silica.

For application, the two pastes are mixed together in a weight ratio of 4:1, placed on a suitable impression tray and introduced as usual into the mouth. After 5 minutes, the rubber elastic molding is removed from the mouth, without leaving residues between the teeth. The impression obtained has a high reproduction resolution.

COMPARATIVE EXAMPLE

The impression paste described in Example 1, without the addition of the oleic acid ethanolamide, is mixed as described therein, in a weight ratio of 4:1 with the initiator paste. Impressions prepared with this mixture are clearly more difficult to remove from the mouth than the nonadhesive material according to Example 1. It was observed that a small interdental flag was torn from the impression and remained in the mouth, as the impression material adhered tightly to the teeth.

EXAMPLE 2

An impression material is prepared by kneading together 800 g of a polyether with aziridino terminal groups, having an average molecular weight of approximately 6500 (the preparation thereof is described in U.S. Pat. No. 3,453,242) and 150 g of fine diatomaceous earth. 24 g of oleic acid ethanolamide were further added.

The impression paste obtained was mixed homogeneously in a weight ratio of 4:1 with the initiator paste described in Example 1. A mouth impression was taken in the usual manner, which was easily removed in a few minutes, no residues remaining in the mouth and an impression of high accuracy being obtained.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A nonadhesive impression material comprising a polyether compound with terminal aziridino groups which crosslink when combined with a polymerization initiator and an adhesion reducing amount of oleic acid ethanolamide.

2. The impression material of claim 1, said material containing 1–15% by weight of oleic acid ethanolamide with respect to the aziridino-polyether present in the material.

3. The impression material of claim 1, said material containing 2–10% by weight of oleic acid ethanolamide with respect to the aziridino-polyether present in the material.

4. The impression material of claim 1, further including a plasticizer.

5. The impression material of claim 4 wherein the plasticizer is a phthalic acid ester, an acylated citric acid ester, a polyglycol, dibenzyltoluene, or a polyethoxylated sorbitan ester.

6. The impression material of claim 4, further including a filler.

7. The impression material of claim 6, wherein the filler is diatomaceous earth, calcium carbonate, calcium silicate, or magnesium oxide.

8. A method of making a dental impression comprising the use of a nonadhesive impression material comprising a polyether compound with terminal aziridino groups which crosslink when combined with a polymerization initiator and an adhesion reducing amount of oleic acid ethanolamide.

9. The method of claim 8 wherein the material contains 1–15% by weight of oleic acid ethanolamide with respect to the aziridino-polyether present in the material.

10. The method of claim 8 wherein the material contains 2–10% by weight of oleic acid ethanolamide with respect to the aziridino-polyether present in the material.

* * * * *